United States Patent [19]
Liu et al.

[11] Patent Number: 5,804,462
[45] Date of Patent: Sep. 8, 1998

[54] METHOD FOR FORMING A MULTIPLE-SENSOR SEMICONDUCTOR CHIP

[75] Inventors: Chung-Chiun Liu, Cleveland Heights; Xiaodong Wang, Cleveland, both of Ohio; Henry G. Hughes, Scottsdale, Ariz.

[73] Assignee: Motorola, Inc., Schaumburg, Ill.

[21] Appl. No.: 565,285

[22] Filed: Nov. 30, 1995

[51] Int. Cl.$^6$ .................................................. H01L 29/84
[52] U.S. Cl. ............................ 438/53; 438/702; 438/745
[58] Field of Search ............................... 438/53, 54, 745, 438/702, 928, 977, 514, 137, 409, 103, 118; 148/DIG. 136; 257/417, 418, 419; 324/760, 765; 73/204.25, 204.26

[56] References Cited

U.S. PATENT DOCUMENTS

| | | | |
|---|---|---|---|
| 4,618,397 | 10/1986 | Shimizu et al. | 156/628 |
| 4,784,721 | 11/1988 | Holmen et al. | 338/42 |
| 4,897,360 | 1/1990 | Guckel et al. | 148/DIG. 25 |
| 5,110,373 | 5/1992 | Mauger | 148/DIG. 159 |
| 5,237,867 | 8/1993 | Cook et al. | 73/204.15 |
| 5,265,417 | 11/1993 | Visser et al. | 60/274 |
| 5,446,437 | 8/1995 | Bantien et al. | 338/25 |
| 5,451,371 | 9/1995 | Fisher et al. | 422/51 |
| 5,632,954 | 5/1997 | Mirza et al. | 438/53 |
| 5,646,072 | 7/1997 | Maudie et al. | 437/228 |
| 5,672,551 | 9/1997 | Fung | 437/901 |
| 5,707,148 | 1/1998 | Visser et al. | 73/25.05 |

FOREIGN PATENT DOCUMENTS

| | | | |
|---|---|---|---|
| 56-164582 | 12/1981 | Japan | 257/419 |
| 6232422 | 8/1994 | Japan | 257/419 |

*Primary Examiner*—John Niebling
*Assistant Examiner*—S. Mulpuri
*Attorney, Agent, or Firm*—Daniel R. Collopy

[57] ABSTRACT

A process for forming different types of sensors, including metal oxide (10), calorimetric (44), and heterojunction (48), on the same semiconductor chip includes the steps of doping a top surface of a silicon substrate (16) with boron to form a diffusion region (18) for a resistive heater, forming a first silicon nitride layer (24) on the diffusion region, forming a first metal layer (26) on the first silicon nitride layer to provide a resistive temperature detector, forming a second silicon nitride layer (28) on the first metal layer, forming a second metal layer (34) on the second silicon nitride layer, and etching a sensing cavity (40) underneath and adjacent to the diffusion region using an anisotropic wet etchant and the diffusion region as an etch-stop. A metal oxide layer (36) is formed over the second metal layer for a metal oxide or heterojunction sensor. The sensor can optionally be suspended by tethers (38) within the sensing cavity.

41 Claims, 4 Drawing Sheets

METHOD FOR FORMING A MULTIPLE-SENSOR SEMICONDUCTOR CHIP

BACKGROUND OF THE INVENTION

The present invention relates, in general, to sensor devices and, more particularly, to an improved method for forming multiple sensors on a single semiconductor chip.

Sensors of various types have previously been formed on silicon wafers. These types include metal-oxide, calorimetric, and humidity sensors. Previously, each such type of sensor has been formed on a separate semiconductor chip due to the lack of a practical, cost-effective process for integrating more than one such type of sensor on the same chip. However, many sensing applications call for the use of more than one type of sensor, and thus require several sensor chips. Such use of several chips is a disadvantage because it increases the manufacturing expense and packaging size of the application. Therefore, there is a need for an improved process for integrating various sensor types onto the same chip.

SUMMARY OF THE INVENTION

In carrying out the objects of the present invention, in one form there is provided a method for forming a sensor. The method comprises the step of doping a top surface of a semiconductor substrate to provide a diffusion region for a resistive heater. The method then comprises the steps of forming a first dielectric layer on the diffusion region, forming a first metal layer on the first dielectric layer, forming a second dielectric layer on the first metal layer, and forming a second metal layer on the second dielectric layer, In addition, the method comprises the step of forming a sensing cavity underneath and adjacent to the diffusion region.

In another form there is provided a method for forming a sensor on a semiconductor chip. The method comprises the step of doping a top surface of a silicon substrate with boron to provide a diffusion region for a resistive heater. Thereafter the method comprises the steps of forming a first silicon nitride layer on the diffusion region, forming a first metal layer on the first silicon nitride layer, forming a second silicon nitride layer on the first metal layer, and forming a second metal layer on said second silicon nitride layer. In addition, the method comprises the step of etching a sensing cavity underneath and adjacent to the diffusion region using an anisotropic wet etchant.

In a further form, there is provided a method for forming a sensor comprising the steps of doping a top surface of a semiconductor substrate to form a resistive heater for the sensor and forming a cavity underneath and adjacent to the resistive heater. The method also comprises the steps of forming a first silicon nitride layer on the resistive heater, forming a resistive temperature detector for the sensor on the first silicon nitride layer, forming a second silicon nitride layer on the resistive temperature detector, and forming a second metal layer on the second silicon nitride layer.

DETAILED DESCRIPTION OF THE DRAWINGS

FIGS. 1–5 are cross-sectional views illustrating the manufacture of a metal-oxide sensor 10 (see FIG. 5) using a new multiple-sensor integration process according to the present invention. Although this new process is primarily illustrated herein with respect to the manufacture of a metal-oxide type sensor, one of skill in the art will appreciate that this process can also be used to form a wide variety of other sensor types on the same chip, as explained further below.

Figure 1:
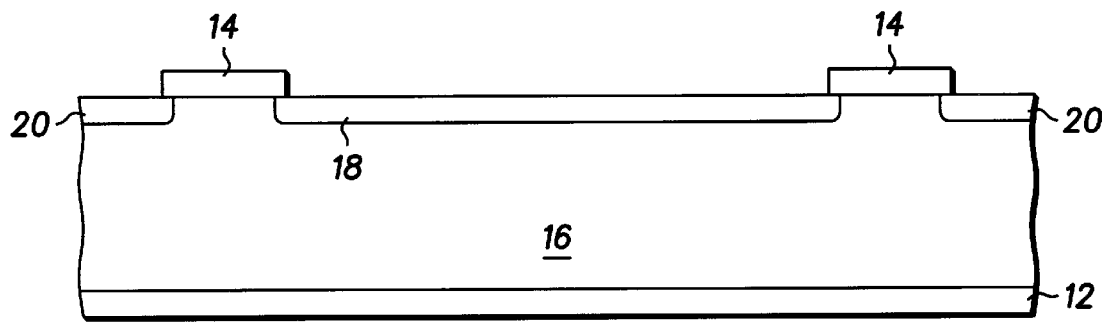
FIGS. 1–5 are cross-sectional views illustrating the manufacture of a metal-oxide sensor according to the method of the present invention.

FIG. 1 illustrates a first stage in the manufacture of a metal-oxide sensor 10, used for example in chemical sensing of carbon monoxide, hydrocarbons, or nitrogen dioxide, which is formed on the same semiconductor chip (e.g. an integrated circuit) as other sensors such as calorimetric and heterojunction sensors. Sensor 10 is made by forming silicon oxide layers 12 and 14 on a silicon substrate 16, for example, by thermal oxidation to a thickness of about 5,000 angstroms. Because portions of substrate 16 will be boron-doped later in the process, substrate 16 initially has an N-type conductivity. Oxide layer 14 is conventionally patterned, for example, by optical lithography and wet etching with buffered hydrofluoric acid (BHF) to provide a diffusion mask. Oxide layer 14 is then used to form P+ diffusion regions 18 and 20 by doping with boron. P+ diffusion region 18 will be used as both a resistive heater and a mechanically supporting frame in the final device (i.e. it supports overlying sensor components formed during later processing).

Figure 2:
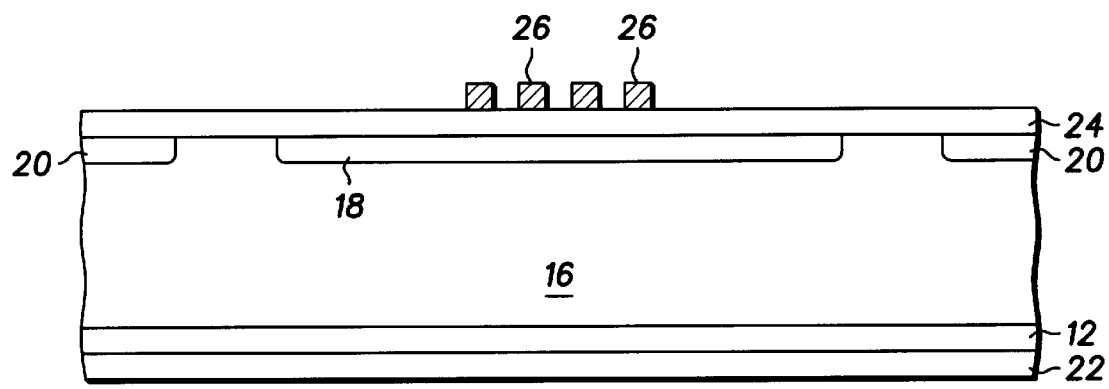

In FIG. 2, oxide layer 14 has been removed, and low-tensile-stress silicon nitride layers 22 and 24 have been formed by, for example, low-pressure chemical vapor deposition (LPCVD) to a thickness of about 5,000 angstroms. Low tensile stress is important for a multilayer structure which is to be operated at elevated temperatures so that it does not crack. Alternatively, nitride layers 22 and 24 can be deposited without removing oxide layer 14. A patterned metal layer 26 is formed, for example, by sputtering titanium to a thickness of about 100 angstroms followed by platinum to a thickness of about 1,000 angstroms. Metal layer 26 is conventionally patterned using, for example, a lift-off process. Alternatively, layer 26 can be patterned by ion milling. For ion milling, a patterned, low-stress silicon nitride layer (not shown) can be used as a milling mask, which does not need to be removed after the ion milling. This nitride can be formed, for example, by plasma enhanced chemical vapor deposition (PECVD) and patterned by optical lithography and reactive ion etching (RIE). Metal layer 26 will be used as a resistive temperature detector (RTD) for sensor 10. Also, silicon nitride layer 24 acts in part as a dielectric layer in sensor 10.

Figure 3:
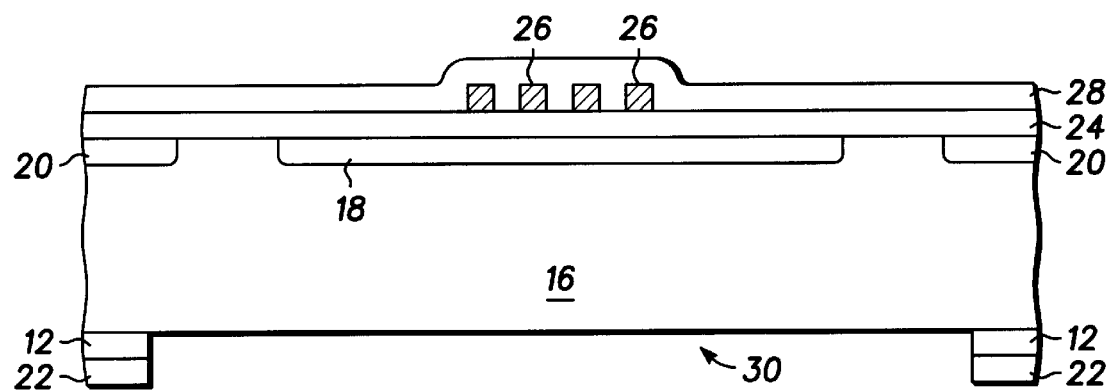

Referring to FIG. 3, a silicon nitride dielectric layer 28 is formed, for example, by PECVD to a thickness of about 3,500 angstroms. As an alternative, a low-stress PECVD oxide layer may be formed instead for dielectric layer 28. Then, oxide layer 12 and nitride layer 22 on the backside of substrate 16 are patterned to open a window 30, which will later be used to etch cavities in substrate 16. This patterning can be done using conventional infrared double-side alignment and RIE (or alternatively, plasma etching).

Figure 4:
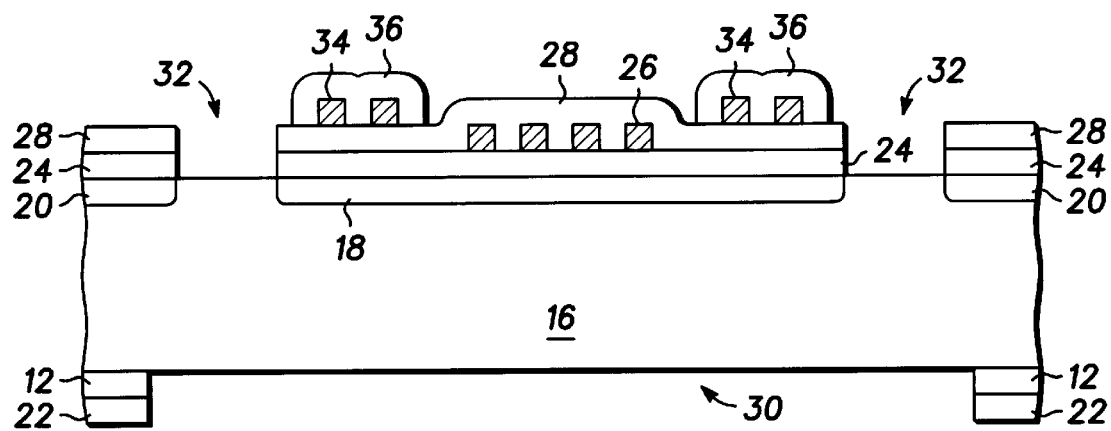

Now, in FIG. 4, openings 32 are formed in nitride layers 24 and 28 by, for example, using photopatterning and RIE. Openings 32 are later used in the formation of a suspended platform 39 following the etching of a cavity 40 (see FIGS.

5 and 6) and also for making electrical contact to P+ diffusion region 20 and metal layer 26. The electrical contacts to region 20 and metal layer 26 are made through additional openings 32 (not shown) on a different portion of substrate 16 which is not shown in the figures.

Next, a patterned metal layer 34 is formed, for example, by conventional sputtering of chromium to a thickness of about 200 angstroms followed by sputtering of gold to a thickness of about 6,000 angstroms and then patterning using conventional wet etching. Metal layers 34 will be used as contact electrodes in sensor 10 (and also for contact electrodes in other sensors formed on the same chip) to contact P+ diffusion region 20 and metal layer 26 through openings 32 as discussed earlier.

A patterned metal oxide layer 36 is formed by, for example, sputtering of tin oxide to a thickness of about 1,000–3,000 angstroms. Patterning of layer 36 can be done by a conventional lift-off process, for example, using ultrasonic waves and an acetone solvent. Alternatively, conventional ion milling or plasma etching can be used to pattern layer 36.

Figure 5:
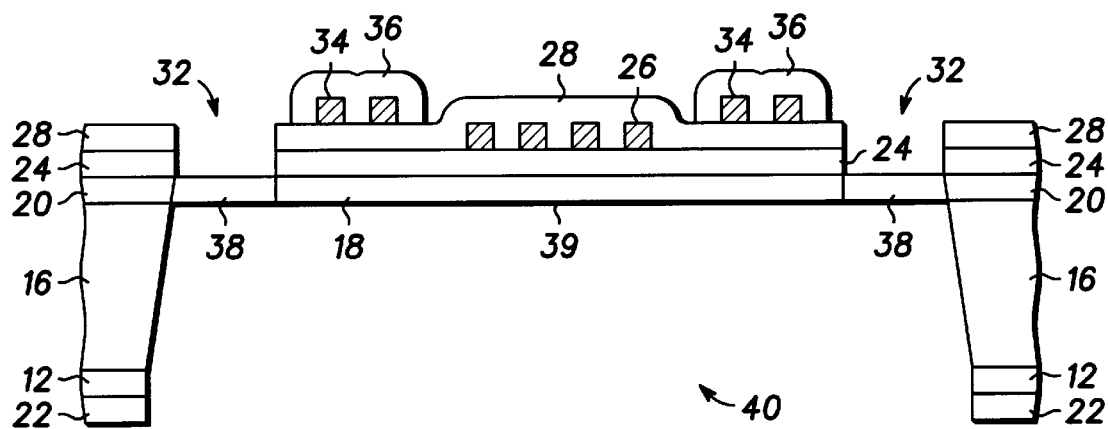

Finally, the processing of sensor 10 is completed as illustrated in FIG. 5 by etching cavity 40 into substrate 16 from its backside using oxide and nitride layers 12 and 22 as a mask. This etching is preferably performed by anisotropic wet etching using conventional bulk micro-machining techniques with an etchant such as tetramethylammoniumhydroxide (TMAH), and substrate 16 preferably has a crystallographic orientation of <100>. During backside etching of cavity 40, the front side of sensor 10 is protected, for example, by black wax or a mechanical fixture, as is known. As an alternative to etching with TMAH, potassium hydroxide (KOH) or ethylenediamine pyrocatechol (EDP) can be used. An example of a preferred EDP formula is a mixture of 1,000 ml ethylenediamine, 320 grams pyrocatechol, 320 ml water, and 6 grams pyrazine. Pyrazine is optional in this mixture.

P+ diffusion regions 18 and 20 are used as an etch stop during the above etch. This can be accomplished because heavily boron-doped silicon has a significantly slower etch rate than lightly-doped silicon when using EDP, KOH, or TMAH as an etchant. The end result of this etch is the suspension of the central portion of sensor 10 on suspended platform 39 within cavity 40 by tethers 38 (see also FIG. 6). In FIG. 5, it should be appreciated that tethers 38 are not in the same cross-sectional plane as diffusion regions 18 and 20, but are instead removed from and behind this plane as further illustrated in FIG. 6. Tethers 38 have been heavily boron-doped in the same P+ diffusion step used to dope diffusion regions 18 and 20 above, and thus tethers 38 are not etched away during the formation of cavity 40. Also, it should be noted that for simplicity no other layers are shown on tethers 38 in FIG. 5. In an actual sensor, however, the top surfaces of tethers 38 also have nitride, titanium-platinum, and chromium-gold layers on them as formed in the process steps described above.

Figure 6:
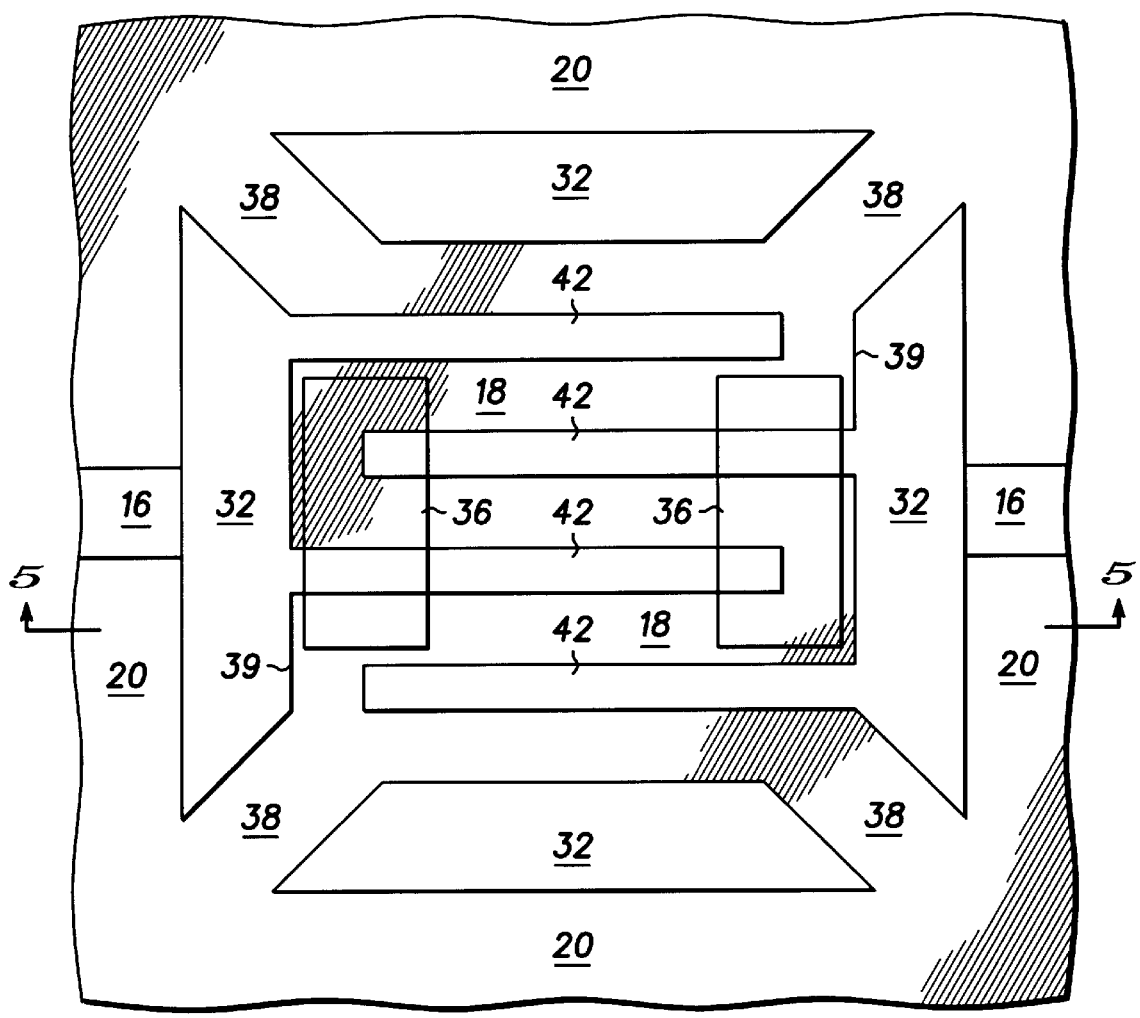
FIG. 6 is a top layout view of the sensor shown in FIG. 5.

FIG. 6 is a top layout view of the sensor shown in FIG. 5. For simplicity, the only layout patterns shown in FIG. 6 correspond to metal oxide layer 36 and P+ diffusion regions 18 and 20 in substrate 16. Other features of sensor 10 not shown here are of conventional structure. Several strips 42 are provided in the layout pattern for P+ diffusion region 18. Strips 42 are portions of sensor 10 that will not be heavily boron-doped with a P+ diffusion, thereby giving diffusion region 18 a corrugated-like shape following the etching of cavity 40 as described earlier. The corrugated shape results from the removal of lightly-doped silicon during this etch. Diffusion region 20 corresponds to P+ regions on the opposite side of tethers 38, but it should be noted that tethers 38 are also heavily boron-doped, as mentioned above. Diffusion region 18 is used as a heater for sensor 10 and also provides a foundation for platform 39.

Openings 32 in FIG. 6 extend fully through substrate 16 because no P+ diffusion was earlier defined in the regions of substrate 16 underlying to openings 32. Openings 32 allow air or another media to enter sensor 10 from the top-side of substrate 16, down through openings 32, and to contact the back-side of sensor 10.

Although the use of tethers 38 to provide suspended platform 39 has been shown above, one of skill in the art will recognize that the novel integration process according to the present invention can also be used where the central portion of sensor 10 is supported by a thin nitride diaphragm. This alternate structure can be formed by modifying the above process to leave nitride layers 24 and 28 intact (i.e., openings 32 are not etched to suspend a sensor platform). Then, the portions of substrate 16 underneath nitride layers 24 and 28 are removed during the etching of cavity 40 to provide a thin diaphragm formed of nitride layers 24 and 28.

The manufacture of one particular sensor type, a metal-oxide sensor, has been illustrated above. However, the method of the present invention can also be used to form other types of sensors on the same chip by the selective use of substantially the same processing steps as described above. As examples of this, the formation of a calorimetric sensor and a heterojunction sensor are described below.

Figure 7:
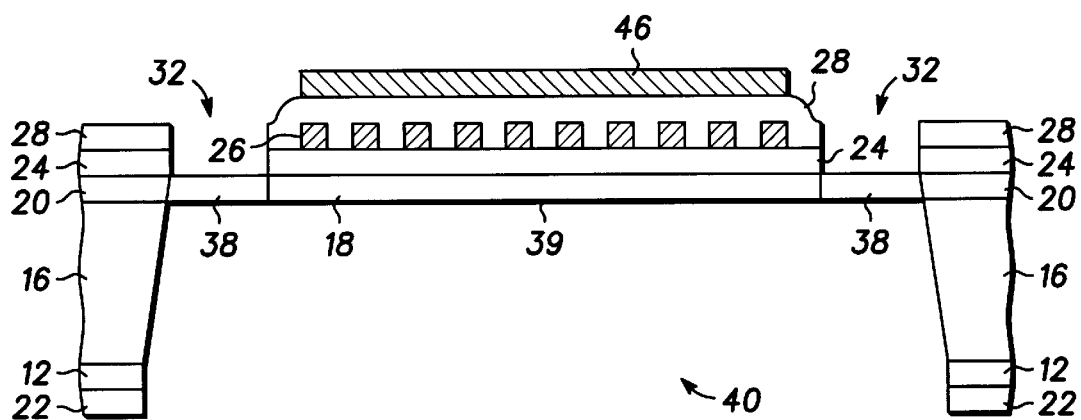
FIG. 7 is a cross-sectional view of a calorimetric sensor.

FIG. 7 illustrates a cross-sectional view of a calorimetric sensor 44 that is formed on the same chip as metal-oxide sensor 10. Prior reference numerals are used for substantially similar elements from FIGS. 1–6. To form sensor 44, processing proceeds as described for FIGS. 1–3 above. Then, openings 32 and metal layer 34 (not shown in FIG. 7) are formed as for FIG. 4 above. It should be noted that metal layer 34 is not shown in FIG. 7, but it still makes contact to portions of metal layer 26 and diffusion region 20 that are found on a different region of substrate 16, which is not located on platform 39. Finally, a catalyst layer 46 is formed on nitride layer 28. It should also be noted that patterned metal layer 26 differs in layout in this sensor 44 than for sensor 10 above, but metal layer 26 is otherwise processed as described above.

Calorimetric sensor 44 is formed to have both a reference element and a corresponding sensing element (these elements are not shown). Each of these elements has a separate P+ silicon heater and platinum temperature sensor built on a suspended platform. The element to be used for sensing is coated with a catalyst as described above. The remaining layout for calorimetric sensor 44 is conventional.

Many materials can be used for catalyst layer 46. Palladium is preferably used. When palladium is used, an adhesive layer such as chromium can be first used to promote adhesion to nitride layer 28. The selected catalyst is preferably sputtered onto nitride layer 28 to a thickness of about 1,000–2,000 angstroms and patterned, for example, using a conventional photoresist lift-off process. Alternatively, a catalyst can be deposited by conventional electron-beam or thermal evaporation and patterned by wet etching or ion milling. Spin-on coating and electroplating are additional options for the formation of certain types of catalysts. Following the formation of catalyst layer 46, sensor 44 is completed as shown in FIG. 7 by performing anisotropic etching to form cavity 40 and tethers 38 as described above.

Figure 8:
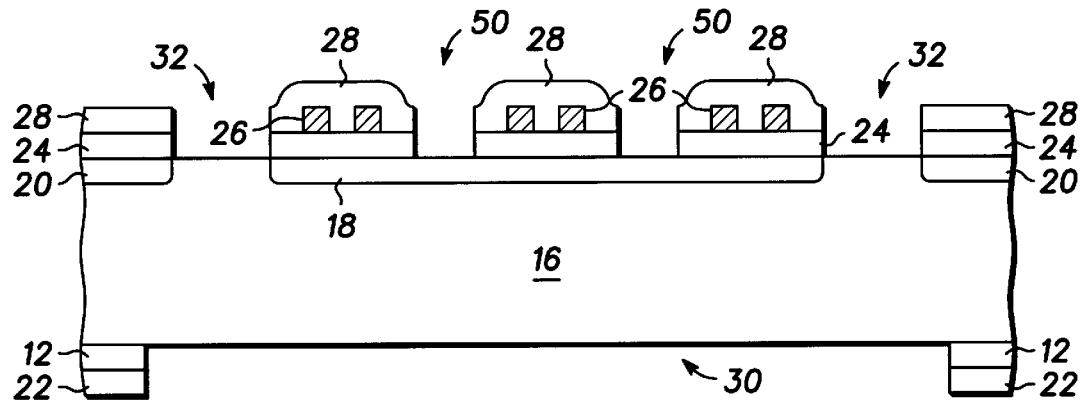
FIGS. 8 and 9 are cross-sectional views illustrating the formation of a heterojunction sensor.
Figure 9:
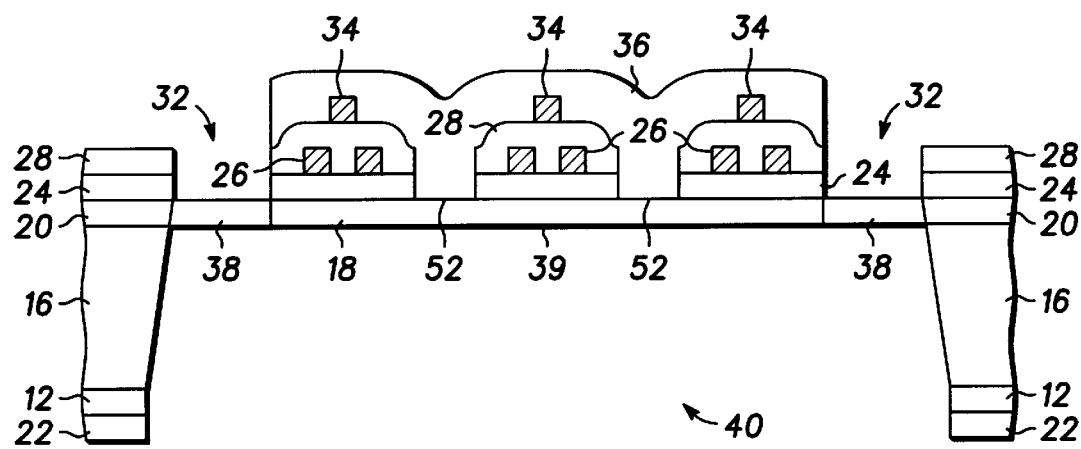

FIGS. 8 and 9 are cross-sectional views illustrating the formation of a heterojunction sensor 48, which is also useful for sensing gases, on the same chip as sensors 10 and 44 above. Prior reference numerals are used for substantially similar elements from FIGS. 1–6. As shown in FIG. 8, processing for sensor 48 proceeds substantially as described for FIGS. 1–3 above with modifications in the layout for metal layer 26 as shown. Next, openings 32 are formed as above for FIG. 4. However, in addition, junction openings 50 are also formed in the same processing step so as to expose the surface of P+ diffusion region 18.

In FIG. 9, metal layer 34 and metal oxide layer 36 are formed substantially as before, except that metal oxide layer 36 now extends down into openings 50 (see FIG. 8) to contact P+ diffusion region 18, thereby providing heterojunctions 52 at the metal oxide-silicon interface. Finally, etching is done to form cavity 40 as above to provide sensor 48.

One of skill in the art will recognize that still other sensors can be formed on the same chip using the method of the present invention. These include pressure sensors, humidity sensors, mass flow sensors, and temperature sensors.

Thus, a novel process for integrating several different types of sensors on the same chip has now been described. This process will reduce the manufacturing expense for multiple sensor applications and will minimize its required packaging size. Further, a single chip can now be used to monitor the same gas environment using sensors of different types to confirm the accuracy and/or indications of other sensors on the chip as cross-reference checks against false measurements.

The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

We claim:

1. A method for forming a sensor, comprising the steps of:
   doping a top surface of a semiconductor substrate to provide a diffusion region for a resistive heater;
   forming a first dielectric layer on said diffusion region;
   forming a first metal layer on said first dielectric layer;
   forming a second dielectric layer on said first metal layer;
   forming a second metal layer on said second dielectric layer; and
   forming a sensing cavity underneath and adjacent to said diffusion region.

2. The method of claim 1 wherein said step of forming said cavity includes etching said semiconductor substrate using said diffusion region as an etch-stop.

3. The method of claim 2 wherein a central portion of said diffusion region is a resistive heater for said sensor.

4. The method of claim 3 wherein said resistive heater has a corrugated shape.

5. The method of claim 1 further comprising the steps of forming a bottom silicon nitride layer on a bottom surface of said semiconductor substrate, patterning said bottom silicon nitride layer to provide a window, and wherein said step of forming said cavity includes etching said cavity through said window.

6. The method of claim 5 wherein said step of patterning said bottom silicon nitride layer is performed prior to said step of forming said second metal layer on said second dielectric layer.

7. The method of claim 6 further comprising the step of forming a bottom silicon oxide layer on said semiconductor substrate prior to said step of forming said bottom silicon nitride layer.

8. The method of claim 1 wherein said step of doping comprises doping with boron.

9. The method of claim 8 further comprising the step of forming, prior to said step of forming said cavity, a plurality of openings extending through said second dielectric layer and said first dielectric layer to expose said semiconductor substrate, and wherein said step of forming said cavity includes forming a plurality of tethers from a portion of said diffusion region adjacent to said plurality of openings to suspend a central portion of said diffusion region in said cavity.

10. The method of claim 9 wherein said step of forming a plurality of openings is performed prior to said steps of forming said second metal layer and forming said cavity.

11. The method of claim 1 wherein said first metal layer comprises a resistive temperature detector.

12. The method of claim 1 wherein said semiconductor substrate is silicon, said first dielectric layer is silicon nitride, and said second dielectric layer is silicon nitride.

13. The method of claim 12 wherein said first metal layer comprises platinum.

14. The method of claim 13 wherein said first metal layer comprises a platinum layer disposed on a titanium layer.

15. The method of claim 12 wherein said step of doping comprises doping with boron.

16. The method of claim 15 wherein said step of forming said cavity comprises etching with an etchant comprising at least one member of the group consisting of tetramethylammoniumhydroxide, potassium hydroxide, and ethylenediamine pyrocatechol.

17. The method of claim 12 wherein said second metal layer comprises gold.

18. The method of claim 12 wherein said second metal layer comprises a gold layer disposed on a chromium layer.

19. The method of claim 1 wherein said step of forming said first dielectric layer comprises forming a silicon nitride layer by low-pressure chemical vapor deposition.

20. The method of claim 19 wherein said step of forming said second dielectric layer comprises forming a silicon nitride layer by plasma-enhanced chemical vapor deposition.

21. The method of claim 1 further comprising the step of forming a metal oxide layer over said second metal layer and in contact with said second dielectric layer.

22. The method of claim 21 wherein said metal oxide layer comprises tin oxide.

23. The method of claim 1 further comprising the step of forming a catalyst layer on said second dielectric layer.

24. The method of claim 23 wherein said sensor is a calorimetric sensor.

25. The method of claim 23 wherein said catalyst layer comprises palladium.

26. The method of claim 23 wherein said catalyst layer comprises a palladium layer on a chromium layer.

27. The method of claim 1 further comprising the step of forming a junction opening extending through said second dielectric layer and said first dielectric layer to expose said diffusion region.

28. The method of claim 27 wherein said step of forming said junction opening is performed prior to said step of forming said second metal layer.

29. The method of claim 28 further comprising the step of forming a metal oxide layer over said second metal layer and in contact with said second dielectric layer, said metal oxide layer further contacting said diffusion region through said junction opening.

30. The method of claim 29 wherein said metal oxide layer is tin oxide.

31. The method of claim 30 wherein said second metal layer comprises gold.

32. A method for forming a sensor on a semiconductor chip, comprising the steps of:

doping a top surface of a silicon substrate with boron to provide a diffusion region for a resistive heater;

forming a first silicon nitride layer on said diffusion region;

forming a first metal layer on said first silicon nitride layer;

forming a second silicon nitride layer on said first metal layer;

forming a second metal layer on said second silicon nitride layer; and etching a sensing cavity underneath and adjacent to said diffusion region using an anisotropic wet etchant.

33. The method of claim 32 further comprising the steps of forming, prior to said step of forming said second metal layer, a bottom silicon nitride layer on a bottom surface of said silicon substrate and patterning said bottom silicon nitride layer to provide a window that exposes a portion of said silicon substrate, wherein said step of etching said cavity includes etching said cavity through said window.

34. The method of claim 32 further comprising, prior to said steps of forming said second metal layer and etching said cavity, forming a plurality of openings through said second silicon nitride layer and said first silicon nitride layer.

35. The method of claim 34 wherein said step of forming said first silicon nitride layer comprises low-pressure chemical vapor deposition and said step of forming said second silicon nitride layer comprises plasma-enhanced chemical vapor deposition.

36. The method of claim 34 wherein said first metal layer comprises platinum.

37. The method of claim 34 wherein said second metal layer comprises gold.

38. The method of claim 34 further comprising the step of forming a metal oxide layer over said second metal layer and in contact with said second silicon nitride layer.

39. The method of claim 34 further comprising the step of forming a catalyst layer on said second silicon nitride layer.

40. The method of claim 34 further comprising the steps of:

forming, prior to said step of forming said second metal layer, a junction opening extending through said second silicon nitride layer and said first silicon nitride layer to expose said diffusion region; and forming a metal oxide layer over said second metal layer and in contact with said second silicon nitride layer, said metal oxide layer further contacting said diffusion region through said junction opening.

41. A method for forming a sensor, comprising the steps of:

doping a top surface of a semiconductor substrate to form a resistive heater for said sensor;

forming a cavity underneath and adjacent to said resistive heater;

forming a first silicon nitride layer on said resistive heater;

forming a resistive temperature detector for said sensor on said first silicon nitride layer;

forming a second silicon nitride layer on said resistive temperature detector; and forming a second metal layer on said second silicon nitride layer.

* * * * *